United States Patent [19]  [11] 4,039,555
Sahm et al.  [45] Aug. 2, 1977

[54] BENZOFURAN DERIVATIVES, PROCESS FOR PREPARING THEM AND THEIR USE AS OPTICAL BRIGHTENERS

[75] Inventors: Wilfried Sahm, Kelkheim, Taunus; Erich Schinzel, Hofheim, Taunus; Günter Rösch, Altenhain, Taunus, all of Germany

[73] Assignee: Hoechst Aktiengesellschaft, Frankfurt am Main, Germany

[21] Appl. No.: 631,928

[22] Filed: Nov. 14, 1975

Related U.S. Application Data

[63] Continuation-in-part of Ser. No. 440,335, Feb. 7, 1974, abandoned.

[30] Foreign Application Priority Data

Feb. 9, 1973    Switzerland ............... 1881/73

[51] Int. Cl.$^2$ ........................................... C07D 271/10
[52] U.S. Cl. ........................... 260/307 G; 252/301.28; 252/301.24; 542/432; 260/346.22; 260/346.71
[58] Field of Search ................................. 260/307 G

[56] References Cited

U.S. PATENT DOCUMENTS 3,772,373  11/1973  Schlapfer et al. ............... 260/309.2
3,900,419  8/1975   Schlapfer et al. ........... 252/301.2 W

FOREIGN PATENT DOCUMENTS 2,405,063  8/1974  Germany

OTHER PUBLICATIONS

Matsuo et al.–C.A. 78, 45070z (1973).

*Primary Examiner*—Raymond V. Rush
*Attorney, Agent, or Firm*—Connolly and Hutz

[57] ABSTRACT

Condensation of a benzofuran, which is substituted in 2-position by a carboxylic acid hydrazide group bound to the benzofuran nucleus via a bridgemember being in conjugation with the double bonds of the benzofuran, with a benzofuran-2-carboxylic acid halide yields a bisacyl hydrazide which is capable of oxdiazol ring closure while splitting off water. The so-obtained oxdiazoles are optical brighteners, especially for polyester materials.

7 Claims, No Drawings

BENZOFURAN DERIVATIVES, PROCESS FOR PREPARING THEM AND THEIR USE AS OPTICAL BRIGHTENERS

This application is a continuation-in-part of our Application Ser. No. 440,335 filed Feb. 7, 1974 now abandoned.

The present invention relates to new benzofuran derivatives, to a process for preparing them and to their use as optical brighteners.

It is known to prepare symmetrical 2,5-bis-[benzofuryl-(2)]-1,3,4-oxdiazols (DOS 2 031 774) and to use them as optical brighteners for organic materials.

The present invention provides colorless to weakly yellow benzofuran derivatives which, when dissolved, show a fluorescence between about 410 and 450 nm and which correspond to the formula

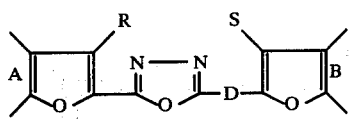
(1)

In this formula

A and B represent aromatic mono-or polynuclear ring systems which are condensed with two adjacent carbon atoms in the manner indicated with the furan nucleus, R and S represent hydrogen or halogen atoms, lower alkyl groups, phenyl groups which may be substituted by lower alkyl, lower alkoxy groups or halogen atoms, or carboxy or sulfo groups which may be modified functionally, D represents a bivalent, aliphatic or aromatic or heteroaromatic bonding member which continues the conjunction.

The aromatic ring systems A and B may contain non-chromophorous substituents, preferably lower alkyl, alkenyl, alkoxy, aryl, preferably phenyl, carboxy or sulfo groups which may be modified functionally, acyl, acylamino or sulfonyl groups and halogen atoms. The above-mentioned groups, which may be identical or different, may be bound singly or in plurality to A or B.

The term "lower" used here in connection with aliphatic radicals shall denote such groups which contain up to 4 carbon atoms.

Under a functionally modified carboxy group mentioned in the definitions for A and B and R and S, there are to be understood at first the salts thereof with colorless cations, the alkali metal or ammonium ions being preferred, furthermore in particular the cyano group, the carboxylic acid ester group or the carboxylic acid amide group. By carboxylic acid ester groups, there are to be understood in particular those of the general formula COOR$^1$, in which R$^1$ represents a phenyl radical or a lower alkyl group which may be branched, and wherein these latter groups and the radical may contain further substituents, for example preferably a low molecular dialkylamino, trialkylammonium or alkoxy group. By a carboxylic acid amide group, there is to be understood in particular a group of the formula CONR$^2$R$^3$, in which the rests R$^2$ and R$^3$ represent hydrogen atoms or lower alkyl groups which may be substituted and which may form together with the nitrogen atom a hydro-aromatic ring, furthermore acid hydrazides of the formula CONHNR$^2$R$^3$, in which R$^2$ and R$^3$ have the meanings given above, and the analogous thio derivatives.

Under a functionally modified sulfo group, there are to be understood, in analogy with the above given definitions, the salts with colorless cations, preferably alkali metal or ammonium ions and furthermore such derivatives in which the SO$_2$ group is bound to a hetero atom such as is the case in the sulfonic acid ester group and in the sulfonamide group. Under sulfonic acid ester group, there is to be understood in particular a group of the formula SO$_2$OR$^1$ in which R$^1$ has the meaning given above, and by a sulfonic acid amide group, there is to be understood a group of the formula SO$_2$NR$^2$R$^3$, in which R$^2$ and R$^3$ have the meanings given above.

Under an acyl group, there is to be understood a group of the formula COR$^4$, in which R$^4$ stands for a preferably lower alkyl radical or phenyl radical, which may be substituted.

Under a sulfonyl radical, there is to be understood in particular a group of the formula SO$_2$R$^5$, in which R$^5$ represents a lower alkyl group or a phenyl group, which may be substituted, these groups containing as the substituents preferably a lower dialkylamino, trialkylammonium, acylamino or sulfo group.

Among the compounds of the general formula (1) those are in particular of interest which correspond to the general formula (2)

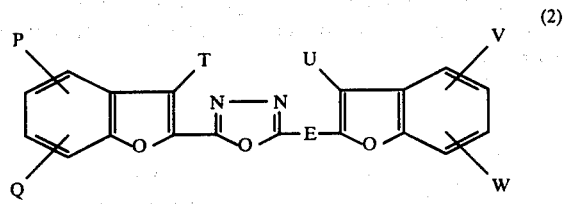
(2)

in which E represents one of the groups indicated below

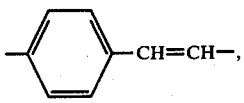 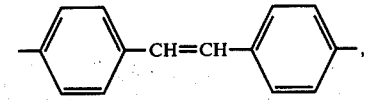

 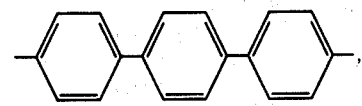

preferably

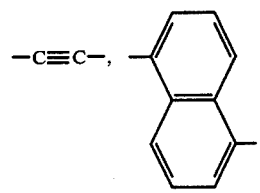

-continued

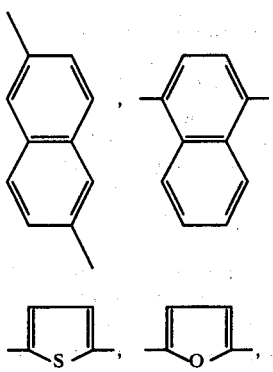

in particular

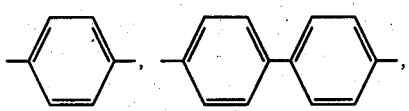

T and U represent, independently of each other, hydrogen or halogen atoms, lower alkyl, carboxy or sulfo groups which may be modified functionally or phenyl groups, P and Q as well as V and W represent, independently of each other, hydrogen or halogen atoms, lower alkyl, alkoxy or phenyl groups, or carboxy or sulfo groups which may be modified functionally or P and Q and V and W together form a lower alkylene group or an annellated benzene nucleus.

Owing to their importance with regard to application, there must be mentioned as particularly outstanding among the compounds of the general formulae (1) and (2) those compounds which correspond to the general formula (3)

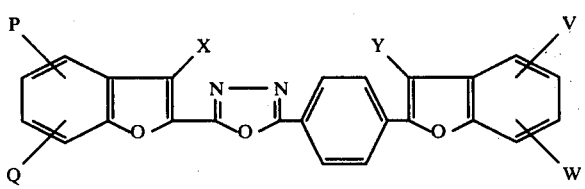

(3)

in which P, Q, V and W have the meanings given in formula (2), and X and Y represent hydrogen atoms or lower alkyl groups.

The benzofuran derivatives of the present invention can be synthetized by several methods. A preferred process is described hereinafter.

1 Mole of a carboxylic acid derivative of the general formula (4)

(4)

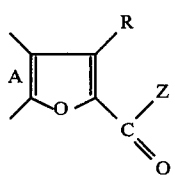

is reacted with 1 mole of a carboxylic acid derivative of the general formula (5)

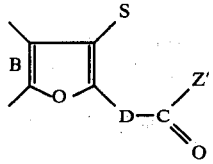

(5)

in which formulae (4) and (5) one of the symbols Z and Z' represents a halogen atom, in particular a chlorine atom, and the other one represents the group —NH—NH$_2$, in inert organic solvents or solvent mixtures, optionally with the use of an acid acceptor, for example a tertiary amine base, at temperatures in the range of from room temperature and about 220° C, to obtain diacylhydrazides of the formula (6)

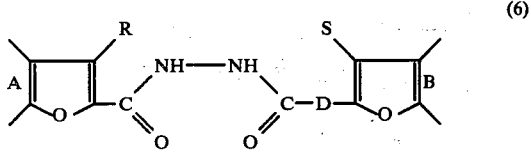

(6)

from which the benzofuran derivatives of the invention and corresponding to the general formula (1) can be prepared by splitting off 1 mole of water. In the formulae (4), (5) and (6), A, B, R, S and D have the meanings given in formula (1).

The oxdiazole ring closures which proceed under separation of water are effected either with de-hydratating agents, for example thionyl chloride, phosphoroxy chloride or polyphosphoric acid, at temperatures in the range of between about 50° C and about 220° C or the diacyl hydrazides of the general formula (6) are heated in inert solvents or solvent mixtures in the presence of acid catalysts, for example organic sulfonic acids, Lewis acids or mineral acids, in particular p-toluene-sulfonic acid, boric acid or ZnCl$_2$.

As inert solvents, there may be used, among others, high-boiling aromatic or aliphatic, optionally halogenated hydrocarbons, for example trichlorobenzenes, dichlorobenzenes, xylenes, etc. or high-boiling esters of aromatic carboxylic acids, for example benzoic acid methyl ester. Normally, the ring closure reactions are effected at temperatures between about 150° C and about 250° C.

As carboxylic acids of the general formula (4a)

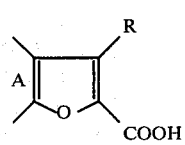

(4a)

on which the acid halides or hydrazides of the formula (4) are based, there may be used, for example with ethyl bromomalonate in the presence of potassium-carbonate.

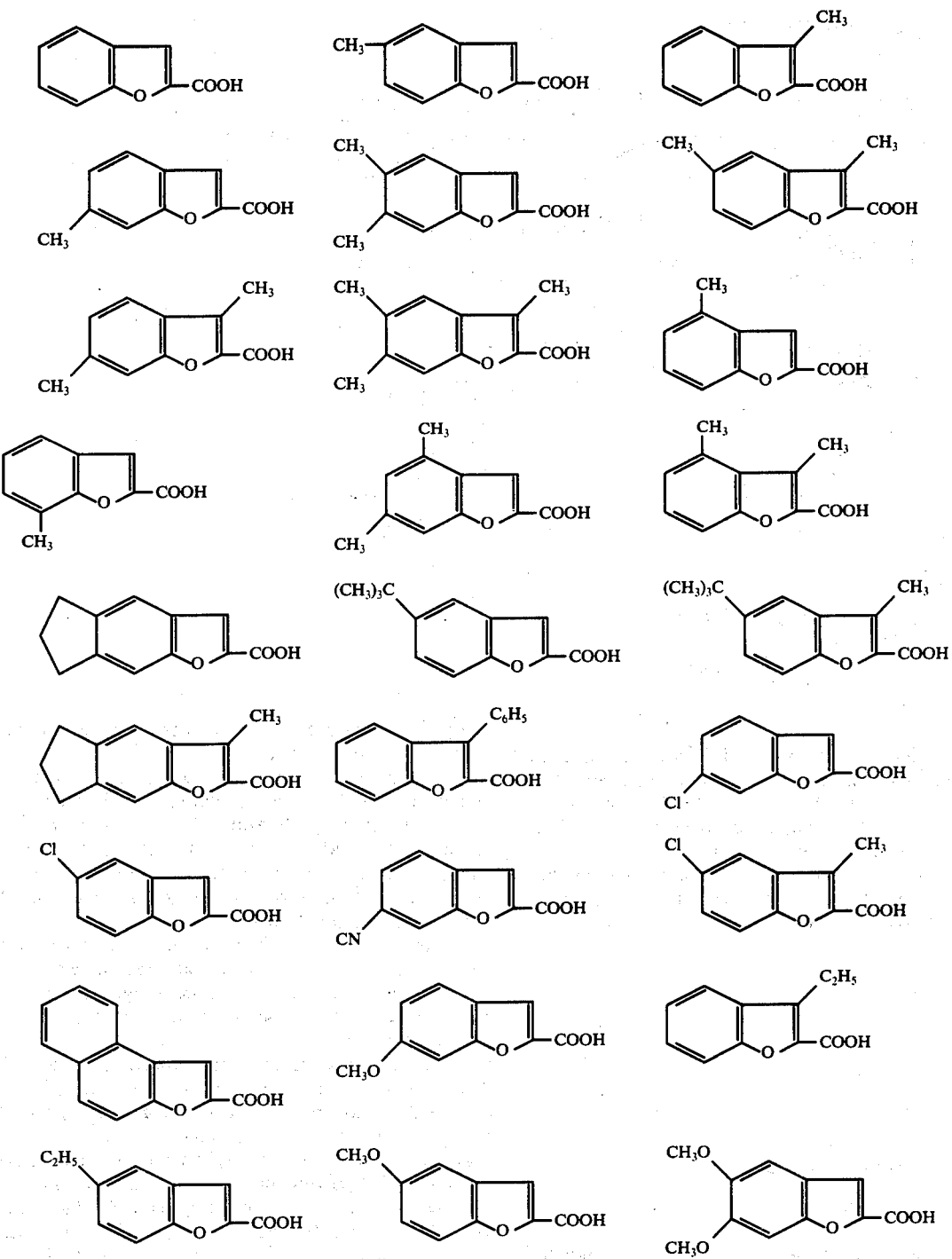

These carboxylic acids of the general formula 4a are prepared according to known methods from a compound of the formula (4b)

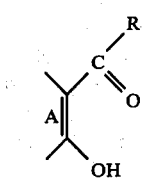
(4b)

As carboxylic acids of the general formula (5a)

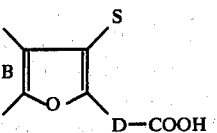
(5a)

on which the acid halides or hydrazides of the formula (5) are based, there may be used, for example:

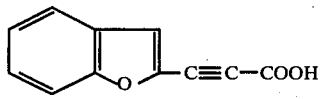
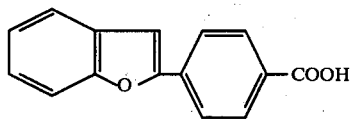
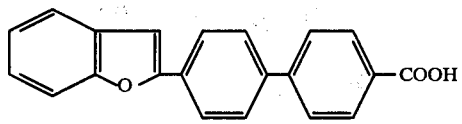
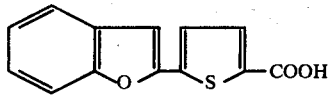
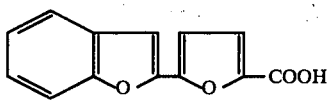
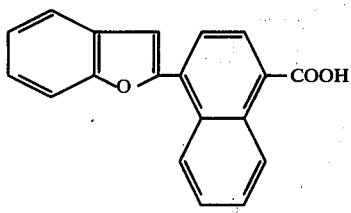
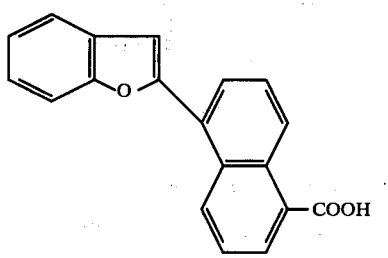
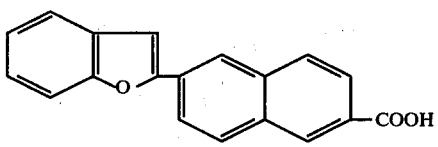

as well as such carboxylic acids of the general formula (5a) which contain instead of the unsubstituted benzofuran nuclei mentioned in the above formulae substituted benzofuran nuclei, for example of the kind indicated in the examples of the carboxylic acids (4a).

These carboxylic acids of the general formula 5a are prepared according to known methods from a compound of the formula (5b)

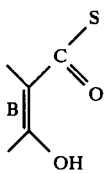

(5b)

and a compound of the formula

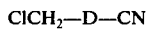

ClCH$_2$—D—CN with subsequent hydrolysation of the cyano group to the carboxylic acid group. The acids of formula 4a and 5a, respectively are easily converted into the corresponding acid chlorides which in turn are reacted with hydrazine to give the products of formula 4 or 5.

It is of course possible to carry out other known transformations in the reaction products obtained according to the present invention, for example sulfonations with sulfonating agents such as H$_2$SO$_4$, mixtures of H$_2$SO$_4$ and SO$_3$ or chlorosulfonic acid or such conversions which lead, for example, starting from molecules containing sulfo or carboxy groups, to compounds with functionally modified sulfo or carboxy groups or the conversion of such groups into other groups of this kind or into the free acids.

Furthermore, there may, for example, also be introduced in known manner chloromethyl groups or methyl groups may be oxidized. In the same manner halogenations and other reactions of the introduced halogen atoms may be carried out, for example the exchange of chlorine or bromine against the —C≡N group or amine functions.

Owing to their strong fluorescence the compounds of the invention have a vast field of application. They may be used, above all, for the optical brightening of the most various synthetic, semi-synthetic and natural high molecular materials.

Under synthetic organic high molecular materials, there are to be understood polymerization products, polycondensation products and polyaddition products and their after-treatment products, for example the polymers on the base of α,β-unsaturated carboxylic acids, of olefin hydrocarbons or of halogenated hydrocarbons (such as polyolefins, polyvinyl chloride, polyvinylidene chloride, polystyrene, polyacrylonitrile, etc.), the polycondensation products on the base of bi- or poly-functional compounds with groups which are capable of being condensed, their products of homo- and co-condensation (such as polyester, polyamides, maleinate resins, polycarbonates, silicone resins etc.), the polyaddition products such as cross-linked or not cross-linked polyurethanes and epoxide resins.

As semi-synthetic organic materials, there may be mentioned, for example cellulose esters and ethers, nitrocellulose, regenerated cellulose and synthetic materials on the base of casein.

Natural organic materials which can be brightened optically are, for example materials of protein such as wool, silk and leather; cellulosic materials such as cotton, paper, wood pulps with fine distribution; furthermore rubber, guttapercha or balata.

The organic materials to be optically brightened may be in the most various stages of processing (crude materials, semi-finished and finished products) or have the most various forms, for example plates, sheets, shaped bodies, chips, granulates, foamed substances, films, foils, lacquers, bands, filaments, fibers, for example in the form of endless filaments, staple fibers, flocks, yarns, strands, twisted yarns, fiber fleeces, felts, wadding, textile fabrics, compound fabrics and knit fabrics, furthermore as powders, mastics, pastes, waxes, adhesive and putty masses, etc.

The new optical brighteners may of course be used everywhere where organic materials of the above-indicated kind are combined with inorganic materials in any manner.

Preferably, however, the compounds of the invention are used for the optical brightening of fibers, textiles, plastics and paper.

The anionic compounds of the invention which are soluble in water are particularly suitable for the optical brightening of native and regenerated cellulose fibers and of wool and synthetic polyamide fibers.

The cationic compounds of the invention which are soluble in water are particularly suitable for the optical brightening of homo- and co-polymers of acrylonitrile, in particular of the commercial copolymers having a minimum content of about 85% of acrylonitrile units.

The compounds of the invention which are insoluble in water and which are particularly suitable for the optical brightening of polyester and polyamide fibers as well as of cellulose and regenerated cellulose fibers may be applied in a solution in organic solvents or in an aqueous dispersion, preferably with the use of dispersing agents. As dispersing agents, there may be used, for example soaps, polyglycol ethers derived from fat alcohols, fatty amines or alkyl phenols, cellulose sulfite waste lyes or condensation products of naphthalene-sulfonic acids which may be alkylated with formaldehyde.

The compounds of the invention are distinguished by the fact that they may be used in the presence of oxidizing and reducing bleaching agents, for example hydrogen peroxide, sodium hypochlorite and sodium chlorite, and sodium dithionite, without the effect of optical brightening being affected. The optical brighteners may be used together with other finishing agents for the purpose of improving the effect or of simplifying the process. Such auxiliary agents are, for example retarders, carriers, dispersants, softeners, compounds having an oleophobic and hydrophobic effect, finishing agents, emulsifiers, washing and wetting agents. The fibrous material so brightened optically, in particular the polyesters of the type of the polyethylene glycol terephthalate shows an excellent fastness to light. Highly brilliant reddish to greenish brightening effects with extraordinarily high whiteness degrees are obtained.

In view of the fact that the compounds of the invention of the formula (1) can be additionally used in the exhaust and thermosol processes, as those described below, in almost all temperature ranges between 60° and 240° C and yield brilliant effects on the most important fibrous materials, they can be considered as being applicable universally.

Particularly good brightening effects are sometimes also obtained when combining the compounds of the invention with other optical brighteners. Such combinations are of interest if shifts of the shade of the brightening effects are to be obtained. Excellent effects are obtained, for example with the combination of the compounds of the invention with the known benzoxazole brighteners of the formula

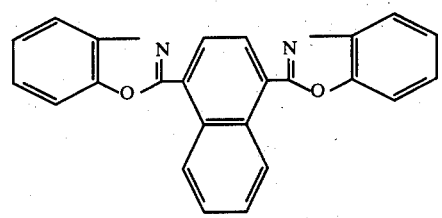

or

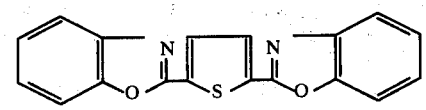

Even brighteners of the cumarine type, naphthotriazole type or distyrylarene are well suitable as mixing components.

The optical brightening of the fibrous material is effected with the aqueous or optionally organic brightener bath either according to the exhaust process at temperatures in the range of preferably about 20° to 150° C or according to thermosoling conditions under which the textile material is brought to a humidity content of about 50 to 120% by impregnation and squeezing or spraying with the solution or the brightener dispersion. The textile material is then subjected to a heat treatment for example about 10 to about 300 seconds, preferably with dry heat at about 120° to about 240° C. This thermosoling process may also be combined with other finishing operations, for example the finishing with synthetic resins in order to obtain easy handling. The optical brighteners of the invention are distinguished by a high stability to the catalysts and additives such as magnesium chloride, zinc nitrate or also polyethylene dispersions, used for this purpose.

The benzofurans of the general formula (1) may also be added to detergents. These may contain the usual fillers and auxiliary agents such as alkali metal silicates, alkali metal polyphosphates and polymeta-phosphates, alkali metal borates, alkali metal salts of carboxymethyl cellulose, foam stabilizers such as alkanol-amides of higher fatty acids or complex formers such as soluble salts of ethylene-diamine-tetracetic acid or diethylene-triamine-pentacetic acid, as well as chemical bleaching agents such as perborates or percarbonates. Very good results are also obtained with perborate-containing detergents in the presence of perborate activators. The usual disinfectants used in detergents do not deteriorate the brightening effect of the compounds of the invention.

Furthermore, the compounds of the invention may be added to high molecular organic materials, either prior to or during their shaping. Thus, they may be added to the moulding masses in the preparation of films, foils, bands or shaped bodies or they may be dissolved in the spinning mass prior to spinning. Suitable compounds may also be added prior to the polycondensation or polymerization, as in the case of polyamide-6, polyamide-6,6 or linear polyesters of the type of the polyethylene glycol terephthalate, to the low molecular starting substances.

The compounds of the invention which are substituted by one or, preferably, two carboxy or carboalkoxy groups can be bound to linear polyester molecules and synthetic polyamides by an ester or amide bondage, if they are added under suitable conditions to these materials or, preferably, to their starting substances. Optical brighteners fixed in this manner by a chemical bondage are distinguished by an extraordinarily high fastness to sublimation and to solvents.

Compounds of the invention which are olefinically unsaturated and which contain, in addition to the fluorescing system, at least one polymerizable olefinic double bond may be used for the preparation of fluorescing polymers or mixtures of polymers, by polymerizing them, under maintenance of the fluorescing system, as such or in admixture with other monomeric or polymeric vinyl compounds. These fluorescent polymers can subsequently be mixed with not fluorescent polymers. Polymers brightened optically in such a manner are distinguished by a high degree of whiteness. In addition thereto, a high fastness to sublimation and to solvents is secured by reason of the chemical fixation of the optical brighteners with the polymers.

The quantity of compounds of the formula (1) to be used according to the invention, referred to the material to be brightened optically, may vary within wide limits, depending on the field of application and the effect desired. It can be determined by simple preliminary tests and is in general in the range of from about 0.01 and about 2%.

The following examples illustrate the invention. The temperatures indicated are given in Celsius degrees (centigrades).

EXAMPLE 1

21.9 g of 2-p-cyanophenyl-benzofuran (mp. 141° - 143° C) were stirred into 600 ml of glycol and, after addition of 12 g of potassium hydroxide, the whole was heated while stirring for 15 hours to 165° - 170° C. The mixture was allowed to cool to 120° C and then 250 ml of 2N sulfuric acid were added dropwise. The whole was poured onto 1200 ml of water, the precipitate was filtered off with suction, washed with water and dried under reduced pressure at 60° C. By recrystallization in o-dichlorobenzene, there were obtained 22.6 g of 4-[benzofuryl-(2)]-benzoic acid (11) in the form of colorless flakes; m.p.: 301° - 302° C.

11.8 g of 4-[benzofuryl-(2)]-benzoic acid (11) were suspended in 500 ml of chlorobenzene and combined, while stirring, with 42 ml of thionyl chloride and 5 ml of dimethylformamide. The reaction mixture was kept for 3 hours at 80° C, 5 g of active carbon were added, the whole was heated to 115° - 120° C, filtered and the filtrate was allowed to cool. It was then stirred in an ice bath and the light yellow crystallization product was separated by filtration. It was finally washed with benzene and dried under reduced pressure.

Yield: 97.5 g of 4-[benzofuryl-(2)]-benzoyl chloride (12) Melting point 163° - 165.5° C.

25.6 g of 4-[benzofuryl-(2)]-benzoyl chloride (12), 17.6 g of benzofuran-2-carboxylic acid hydrazide (14) and 13 g of N.N-dimethylaniline were heated for 60 minutes to the boiling temperature in 400 ml of chlorobenzene. The whole was stirred for 30 minutes at 0° C, the precipitate was separated by filtration with suction, washed with chlorobenzene, suspended in water and the adhering chlorobenzene was eliminated by distillation with steam. Then, the whole was again filtered with suction, the white product was washed with water and dried under reduced pressure at 60° C.

Yield: 39.4 g of compound (13), m.p. 258° - 260° C (crude product)

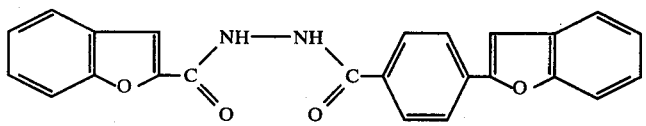

(13)

9.9 g of the diacyl hydrazide (13) were heated together with 0.5 g of p-toluene-sulfonic acid in 150 ml of trichlorobenzene for 90 minutes to 210° - 220° C, during which time about 50 of a mixture of trichlorobenzene and water separated by distillation. After cooling to room temperature, the crystal magma was separated by filtration with suction, washed with benzene and methanol and dried under reduced pressure at 60° C.

Yield: 5.2 g of cmpound (101), m.p. 236° - 238° C.

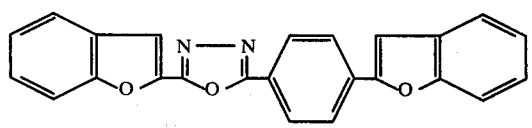

(101)

The compounds indicated in the following Table 1 were prepared in analogous manner.

TABLE 1

| No. | $A_1$ | $A_2$ | $A_3$ | $A_4$ | $A_5$ | $B_1$ | $B_2$ | $B_3$ | $B_4$ | $B_5$ | M.p.° C | M.p.I.P.*° C |
|-----|-------|-------|-------|-------|-------|-------|-------|-------|-------|-------|---------|--------------|
| 101 | H | H | H | H | H | H | H | H | H | H | 236–238 | 260–263 |
| 102 | $CH_3$ | H | H | H | H | H | H | H | H | H | 239–240 | 209–212 |
| 103 | H | H | $CH_3$ | H | H | H | H | H | H | H | 253–254 | 287–292 |
| 104 | H | H | $CH_3$ | $CH_3$ | H | H | H | H | H | H | 281–284 | 274–279 |
| 105 | H | H | $t\text{-}C_4H_9$ | H | H | H | H | H | H | H | 239–244 | 298 Zers. |
| 106 | H | H | H | $OCH_3$ | H | H | H | H | H | H | 256–257 | 229–230 |

TABLE 1-continued

[Structure: benzofuran-oxadiazole-phenyl-benzofuran with substituents A1-A5 and B1-B5]

| No. | A1 | A2 | A3 | A4 | A5 | B1 | B2 | B3 | B4 | B5 | M.p. °C | M.p.I.P.*° C |
|---|---|---|---|---|---|---|---|---|---|---|---|---|
| 107 | H | \<benzo\> | | H | H | H | H | H | H | H | 272–274 | 268–271 |
| 108 | H | H | H | H | H | H | CH₃ | H | H | H | 207–208 | 243–246 |
| 109 | CH₃ | H | H | H | H | H | CH₃ | H | H | H | 245–247 | 182–184 |
| 110 | H | H | CH₃ | H | H | H | CH₃ | H | H | H | 206–208 | 221–224 |
| 111 | H | H | CH₃ | CH₃ | H | H | CH₃ | H | H | H | 253–254 | 225–229 |
| 112 | H | H | t-C₄H₉ | H | H | H | CH₃ | H | H | H | 161–163 | 138–162 |
| 113 | H | \<benzo\> | | H | H | H | CH₃ | H | H | H | 267–269 | 232–237 |
| 114 | H | H | H | H | H | H | CH₃ | H | CH₃ | H | 272–273 | 269–270 |
| 115 | H | H | CH₃ | H | H | H | CH₃ | H | CH₃ | H | 239–241 | 253–254 |
| 116 | H | H | CH₃ | CH₃ | H | H | CH₃ | H | CH₃ | H | 254 | 260–264 |
| 117 | H | \<benzo\> | | H | H | H | CH₃ | H | CH₃ | H | 259–261 | 271–273 |
| 118 | H | H | H | H | H | H | CH₃ | CH₃ | H | CH₃ | H | 220–223 | 243–245 |
| 119 | H | H | CH₃ | CH₃ | H | H | CH₃ | CH₃ | H | CH₃ | H | 233–234 | 258–262 |
| 120 | H | H | H | H | H | H | H | H | CH₃ | H | H | 269–272 | 276–279 |
| 121 | H | H | CH₃ | H | H | H | H | H | CH₃ | H | H | 276–278 | 299–304 |
| 122 | H | H | CH₃ | CH₃ | H | H | H | H | CH₃ | H | H | 269–273 | 258 |
| 123 | H | \<benzo\> | | H | H | H | H | H | CH₃ | H | H | 275 | 301–303 |
| 124 | H | H | H | H | H | H | H | H | CH₃ | CH₃ | H | 261–262 | 272–274 |
| 125 | CH₃ | H | H | H | H | H | H | H | CH₃ | CH₃ | H | 280–283 | 234–239 |
| 126 | H | H | CH₃ | H | H | H | H | H | CH₃ | CH₃ | H | 268–270 | 283–286 |
| 127 | H | H | CH₃ | CH₃ | H | H | H | H | CH₃ | CH₃ | H | 295–298 | 310–312 |
| 128 | H | H | t-C₄H₉ | H | H | H | H | H | CH₃ | CH₃ | H | 239–241 | 283–287 |
| 129 | H | \<benzo\> | | H | H | H | H | H | CH₃ | CH₃ | H | 303–305 | 283–286 Zers. |
| 130 | H | H | H | H | H | H | H | t-C₄H₉ | H | H | 234–237 | 236–239 |
| 131 | H | H | H | H | H | H | H | H | OCH₃ | H | 215–219 | 240–241 |
| 132 | H | H | CH₃ | CH₃ | H | H | H | H | OCH₃ | H | 230 | 179–181 |
| 133 | H | H | H | H | H | H | H | Cl | H | Cl | 253–254 | 309–314 |
| 134 | H | H | CH₃ | CH₃ | H | H | H | Cl | H | Cl | 283–285 | 271–273 |
| 135 | H | \<benzo\> | | H | H | H | H | Cl | H | Cl | 304–305 | 298–301 |
| 136 | H | H | H | H | H | H | \<benzo\> | | H | H | 290–291 | 302–303 |
| 137 | H | \<benzo\> | | H | H | H | \<benzo\> | | H | H | 301–303 | 288–289 |
| 138 | H | H | Cl | H | Cl | H | H | H | H | H | 304–308 | 242 Zers. |
| 139 | H | H | H | OCH₃ | H | H | H | H | H | H | 315–318 | 201–203 |
| 140 | H | H | H | H | H | H | H | H | OCH₃ | H | 278–280 | 250–252 |

*) I.P. = Intermediate product of formula (6)

TABLE 2

[Structure: benzofuran with A1–A5 substituents and —CO—NH—NH₂ group at position 2]

| No. | A1 | A2 | A3 | A4 | A5 | M.p. °C |
|---|---|---|---|---|---|---|
| 14 | H | H | H | H | H | 172–174 |
| 15 | CH₃ | H | H | H | H | 141–142 |
| 16 | H | H | CH₃ | H | H | 159–163 |
| 17 | H | H | CH₃ | CH₃ | H | 171–172 |
| 18 | H | H | t-C₄H₉ | H | H | 137–139 |
| 19 | H | H | H | OCH₃ | H | 129–130 |
| 20 | H | H | Cl | H | Cl | 205–212 |
| 21 | H | \<benzo\> | | H | H | 248–251 |

Compounds in which the benzofuran radicals bear different substituents were obtained, for example by the reaction of (12) or corresponding acid chlorides with the carboxylic acid hydrazides (14) – (21) of Table 2.

When mixing 50 parts of compound (101) with 50 parts of the benzoxazole (200)

(200)

there were obtained 100 parts of the optical brightener (201) cf. Example 2 to 9.

EXAMPLE 2

A fabric of polyethylene glycol terephthalate was impregnated with a bath which contained 1 g/l of one of the optical brighteners indicated below in dispersed form. The textile material treated in this manner was squeezed between rollers until it contained 60% of liquid referred to its dry weight and then subjected to a hot air treatment at 180° C or 160° C. After this treatment, the fabric showed an excellent degree of whiteness compared with that of untreated material. In addition, the goods so brightened had an excellent fastness to light of 6–7 (according to DIN 54004 (German Industrial Standard)).

| Optical Brightener | Whiteness degrees according to Berger | | Whiteness degrees according to Stensby | |
|---|---|---|---|---|
|  | 160° C | 180° C | 160° C | 180° C |
| (101) | 118 | 123 | 125 | 133 |
| (124) | 139 | 149 | 146 | 155 |
| (127) | 122 | 124 | 122 | 128 |
| (201) | 144 | 156 | 144 | 152 |

EXAMPLE 3

A fabric of polyethylene terephthalate was treated, at a goods-to-liquor ratio of 1:20 with a washing bath which contained 6 g/l of a detergent of the following composition:
- 50% of sodium tripolyphosphate,
- 6% of sodium metasilicate,
- 4% of carboxymethylcellulose, salt-containing, viscosity in a 5% solution at 20° C 1500 cP (Hoppler-viscosimeter),
- 10% of isotridecyl alcohol - polyglycol ether (containing on the average 8 ethylene glycol units)
- 0.05% of optical brightener (see below), rest to 100%: $Na_2SO_4$ and traces of water. The fabric was washed for 10 minutes at 60° C, then rinsed and dried. This treatment was repeated up to ten times. The fabric showed a good degree of whiteness and a clear improvement of the whiteness effect as compared to a material washed without brightener.

|  | Whiteness degrees according to Berger |
|---|---|
| Compound (124) | 106 |
| Compound (101) | 99 |

EXAMPLE 4

The process was carried out according to the method described in Example 2, but using a fabric of polyamide.

|  | Whiteness degrees according to Berger |
|---|---|
| Compound (101) | 105 |
| Compound (124) | 107 |

EXAMPLE 5

A yarn of polyethylene glycol terephthalate was introduced at a goods-to-liquor ratio of 1:25 into a bath which contained 0.1% of one of the optical brighteners indicated below and 0.6 g/l of sodium chlorite. The pH-value of the bath was adjusted to 3.5 by means of formic acid. The cold bath was heated within 30 minutes to 85° C and kept for 30 minutes at this temperature. The bath was further heated to 120° C and the material was treated for 30 minutes under these conditions. After rinsing and drying, the yarn showed an excellent degree of whiteness.

| Optical brightener | Whiteness degrees according to Berger | Whiteness degrees according to Stensby |
|---|---|---|
| (101) | 140 | 136 |
| (124) | 141 | 138 |
| (201) | 160 | 164 |

EXAMPLE 6

A fabric of polyamide 6 was treated at a goods-to-liquor ratio with a bath which contained 0.2% of one of the optical brighteners mentioned below. The pH-value of the bath was adjust to 4 with oxalic acid. The cold bath was slowly heated to the boiling temperature and the substrate was treated for 30 minutes. The fabric was then rinsed and further treated in the usual manner.

|  | Whiteness degrees according to Berger |
|---|---|
| Compound (101) | 135 |
| Compound (124) | 149 |

EXAMPLE 7

A fabric of cotton was treated at a goods-to-liquor ratio of 1:20 with a bath which contained 0.25% of one of the optical brighteners mentioned below and 10% of Glauber's salt. The cold bath was heated to 60° C and the fabric to be treated was moved therein for 30 minutes. After rinsing and drying of the material, the following whiteness degrees were measured:

|  | Whiteness degrees according to Berger |
|---|---|
| Compound (101) | 115 |
| Compound (124) | 96 |

EXAMPLE 8

A cotton fabric finished with N,N'-dimethylol-ethyleneurea was impregnated with a bath which contained, in dispersed form, 1 g/l of one of the optical brighteners mentioned below. The textile material so treated was squeezed between rollers until it contained 80% of its dry weight of liquid and then subjected to a hot air treatment at 150° C for 2 minutes. The material so dried showed the following whiteness degrees:

| Optical brightener | Whiteness degrees according to Berger | Whiteness degrees according to Stensby |
|---|---|---|
| (101) | 133 | 137 |
| (124) | 142 | 135 |
| (127) | 142 | 137 |
| (201) | 142 | 140 |

EXAMPLE 9

A fabric of polyethylene glycol terephthalate was treated at a goods-to-liquor ratio of 1:20 with a bath which contained 0.2% of one of the optical brighteners mentioned below and 1% of a commercial carrier on the basis of o-phenyl-phenol. The bath which had a temperature of 50° C was heated within 30 minutes to the boiling temperature and the fabric was treated for 45 minutes at this temperature. The fabric was then rinsed and dried in the usual manner.

| Optical brightener | Whiteness degrees according to Berger | Whiteness degrees according to Stensby |
|---|---|---|
| (101) | 123 | 127 |
| (124) | 142 | 133 |
| (201) | 171 | 154 |

We claim:

1. A compound of the formula

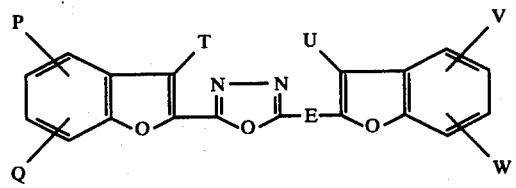

wherein E is p-phenylene, T and U are hydrogen or methyl; P, Q, V and W are hydrogen, chlorine, methyl or methoxy, or P and Q together or V and W together are a benzene ring annellated in the 4,5-position.

2. The compound as defined in claim 1, wherein T and U are hydrogen, P is 6-methoxy and Q, V and W are hydrogen.

3. The compound as defined in claim 1, wherein T and U are hydrogen, P is 5-methyl and Q, V and W are hydrogen.

4. The compound as defined in claim 1, wherein U is methyl and T, P, Q, V and W are hydrogen.

5. The compound as defined in claim 1, wherein V is 5-methyl, W is 6-methyl and T, U, P and Q are hydrogen.

6. The compound as defined in claim 1, wherein T, U, P, Q, V and W are hydrogen.

7. The compound as defined in claim 1, wherein P and Q together are a phenyl ring annellated in 4,5 positions and T, U, V and W are hydrogen.

* * * * *